United States Patent [19]

Farrell et al.

[11] Patent Number: 5,409,915
[45] Date of Patent: Apr. 25, 1995

[54] BIS-PLATINUM (IV) COMPLEXES AS CHEMOTHERAPEUTIC AGENTS

[75] Inventors: Nicholas Farrell, Richmond, Va.; Silvano Spinelli, Monza, Italy; Mariella Valsecchi, Lecco, Italy; Ernesto Menta, Naviglio, Italy

[73] Assignee: The University of Vermont and State Agricultural College, Burlington, Vt.

[21] Appl. No.: 120,434

[22] Filed: Sep. 14, 1993

[51] Int. Cl.⁶ .................. A61K 31/555; A61K 31/28; C07F 15/00
[52] U.S. Cl. .................. 514/187; 514/188; 514/492; 544/64; 544/225; 546/2; 546/11; 546/152; 546/5; 546/6; 548/101; 548/402; 556/137
[58] Field of Search ............... 556/137; 514/492, 187, 514/188; 546/5, 6, 2, 11, 152; 544/64, 225; 548/101, 402

[56] References Cited

U.S. PATENT DOCUMENTS

| | | | |
|---|---|---|---|
| 4,225,529 | 9/1980 | Hydes et al. | 260/429 R |
| 4,250,189 | 2/1981 | Hydes et al. | 424/287 |
| 4,533,502 | 8/1985 | Rochon et al. | 546/8 |
| 4,565,884 | 1/1986 | Andrulis, Jr. et al. | 556/137 |
| 4,571,335 | 2/1986 | Taylor et al. | 424/131 |
| 4,797,393 | 1/1989 | Farrell et al. | 514/188 |
| 5,072,011 | 12/1991 | Abrams et al. | 556/137 |
| 5,107,007 | 4/1992 | Farrell | 556/137 |
| 5,145,848 | 9/1992 | Pasini et al. | 514/185 |

*Primary Examiner*—Jos'acu/e/ G. Dees
*Assistant Examiner*—Porfirio Nazario-Gonzalez
*Attorney, Agent, or Firm*—Burns, Doane, Swecker & Mathis

[57] ABSTRACT

Novel bis(platinum) (IV) complexes coupled via diamine bridging agents are taught as well as methods for their preparation. These complexes are to be used as pharmaceutical agents, e.g., for the treatment of cancer and parasitic diseases.

31 Claims, No Drawings

BIS-PLATINUM (IV) COMPLEXES AS CHEMOTHERAPEUTIC AGENTS

FIELD OF THE INVENTION

The invention relates to novel bis(platinum) (IV) complexes, methods for their preparation, and methods for their use as pharmacological agents, in particular, for treatment of cancer.

BACKGROUND OF THE INVENTION

The clinical use of platinum complexes such as cisplatin and carboplatin in cancer chemotherapy is well established in the art. A number of platinum complexes, such as PLATINOL®, a registered trademark of cisplatin manufactured by Bristol Myers, Co., are used to treat testicular, ovarian, head and neck, and small-cell lung carcinomas. However, treatment with cisplatin may result in severe nephrotoxicity. A further clinical disadvantage is the problem of acquired drug resistance resulting in the minor becoming refractory to treatment by the agent.

To overcome the nephrotoxic effects of cisplatin, a second-generation analog, carboplatin, was developed. PARAPLATIN® is a registered trademark for carboplatin manufactured by Bristol-Myers, Co. Carboplatin, or [Pt(NH$_3$)$_2$ (CBDCA)] (where CBDCA is 1,1'-cyclobutanedicarboxylate), is effective against the same spectrum of carcinomas as cisplatin, but exhibits a marked reduction in the nephrotoxic effects.

A number of different platinum compounds have been developed in an attempt to treat different tumors or carcinomas. For instance, U.S. Pat. No. 4,225,529 discloses the use of a cis coordination compound of platinum having four ligands which are selected from the group consisting of halides, sulphates, phosphates, nitrates, carboxylates, and same or different straight-chain amines which are coordinated to the platinum atom through their nitrogen atoms. These complexes are used for treating L-1210 leukemia in mice.

Also, U.S. Pat. Nos. 4,250,189, 4,553,502, and 4,565,884 relate to various Pt(II) and Pt(IV) complexes having antitumor activity. These bis(platinum) complexes are linked with a carboxylate linkage such that upon administration of these complexes to the patient, the complexes undergo rapid hydrolysis to produce two cis monoplatinum moieties which are then delivered to the active site.

Additionally, PCT WO 88/00947, which corresponds to U.S. Pat. No. 4,797,393, discloses a bis(-platinum) complex which is delivered intact to the active site. This bis(platinum) complex has a bridging diamine or polyamine ligand and has primary or secondary amines or pyridine type nitrogens attached to the platinum complex, as well as two different or identical ligands which may be a halide, sulphate, phosphate, nitrate, carboxylate, substituted carboxylate or dicarboxylate. PCT WO 88/00947 also relates to bis(-platinum) complexes wherein the platinum moieties are linked by a diamine bridging agent, and wherein the platinum moieties are attached to ionic and neutral groups such that the net charge on the two platinum coordination spheres is 2+ or 1+.

However, critical problems still exist which limit the effective use of platinum complexes as therapeutics, most especially their narrow spectrum of activity against different tumors and the development of tumor cells which are resistant to the cytotoxic effects of cisplatin. (Loehrer et at., *Ann, Intern, Med.*, (1984), 100, 704–711). For a general review relating to available platinum analogs, see, Christian, Michael, *Seminars in Oncology*, (1992), 19, 720–733.

It is generally believed that platinum complexes such as cisplatin manifest their biological activity through covalent interaction with DNA. In particular, cisplatin induces the formation of a range of adducts on DNA including monodentate adducts, bidentate adducts, such as GG or AG, and GNG intrastrand crosslinks. (Reedijk et al., *Structure and Bonding*, (1987), 67, 53–89). To a lesser extent, cisplatin also results in interstrand GG crosslinks and DNA-protein crosslinks. (Rahmouni et al., *Biochemistry*, (1987), 26, 7229–7234). These DNA lesions result in conformational changes which are reflected in bending and local unwinding of the DNA. These DNA lesions have been reported to inhibit the activity of various DNA polymerases. (Vallan et at., *Nucl. Acids Res.*, (1988), 16, 4407–4418; Pinto et at., *Proc. Natl. Acad. Sci*, (1985), 82, 4616–4619; and Gralla et al., *Cancer Res.*, (1987), 47, 5092–5096). The interstrand crosslink between two neighboring guanine bases has also been shown to inhibit RNA polymerase function. (Lemaire et al., *Proc. Natl. Acad. Sci.* (1991), 88, 1982–1985). Accordingly, the cytotoxic effects of cisplatin are most likely attributable to the combined effects of these separate DNA lesions, rather than the result of any one specific lesion event.

Mono(platinum) and bis(platinum) complexes respectively containing one or two platinum atoms are known in the art. (See, e.g., U.S. Pat. Nos. 4,225,529, 4,250,189, 4,533,502, 4,565,884, 4,571,335 and 4,797,393). For example, mono(platinum) complexes include monomeric chloramine square-planar Pt(II) compounds which are four coordinate. The relative number of chloride and ammonia groups in such compounds may vary and these compounds may therefore be described by the general formula:

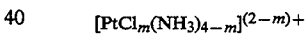

$$[PtCl_m(NH_3)_{4-m}]^{(2-m)+}$$

Thus, the structure of these compounds may vary from [Pt(NH$_3$)$_4$]$^{2+}$ where m=0 to PtCl$_4^{2-}$ where m=4. Since Cl is more substitution labile in comparison to ammonia, the complexes [PtCl$_2$(NH$_3$)$_2$] and [PtCl(NH$_3$)$_3$]Cl are considered bifunctional and monofunctional respectively, wherein the bi and mono prefixes refer to the number of leaving ligands. The charge of the complex is determined by the fact that the Pt(II) cation has a formal charge of +2 and thus requires a negative charge of −2 for charge neutralization. For example, when m=0, neutralization is provided by the presence of two non-coordinating anions, such as chloride anions.

Coordinate bond formation results in electron pairing in the Pt-Cl bond. However, since the ammonia ligand is considered to be neutral, the bonding may be described as electron-pair donation from NH$_3$ to the empty orbitals on the Pt(II) atom. Thus, no electron sharing between the Pt and NH$_3$ group takes place. Because of this absence of electron sharing, the number of neutral ligands does not affect the overall charge in the Pt coordination sphere. Thus, [Pt(NH$_3$)$_4$]$^{2+}$ is formally a 2+ cation requiring a non-coordinating anion or anions, or counter-anions, having a net negative charge of 2- for neutralization of the complex. For example, neutralization can be provided by two mononegatively charged anions (e.g., NO$_3^-$, Cl$^-$, $PF_6^-$, $BF_4^-$, and monocarboxylates having the general formula $RCOO^-$) or a single dinegatively charged anion (e.g., $SO_4^{2-}$, dicarboxylates having the general formula. $(RCOO)_2^{3-}$). Therefore, $[PtCl_2(NH_3)_2]$ is a neutral complex. Moreover, in some cases, Pt(II) anions may serve as counteranions. An example is the well known Magnus salt $[Pt(NH_3)_4]^{2+} [PtCl_4]^{2-}$.

It is noted that anionic ligands such as $Cl^-$ may be either coordinately bound (i.e., forming a Pt-Cl bond) or may act as a counter-anion without any need for covalent bond formation. The exact form that anions such as $Cl^-$ are present in a given platinum complex depends both on theoretical considerations (kinetic vs. thermodynamic effects) and the actual synthetic procedures utilized to make the complex (e.g., the extent of reaction, acidity, concentration of the particular anion, such as the concentration $Cl^-$ which is contained in the reaction mixture). These considerations are applicable to other anionic and neutral ligands as well.

The fact that the overall charge of monoplatinum complexes depends on the relative number of neutral and anionic ligands which are bound to the Pt(II) metal, e.g., $NH_3$ and $Cl^-$ ligands, is also applicable for polynuclear complexes (which contain more than one Pt(II) coordinate spheres), and for Pt(IV) containing complexes wherein the oxidation state of the platinum moiety is 4+. For example, dinuclear complexes where two equivalent Pt(II) coordination spheres are linked by a diamine bridging agent may be represented by the general formula $[\{PtCl_m(NH_3)_{3-m}\}_2 (diamine)]^{2(2-m)+}$. Thus, when m=2, and two bifunctional coordination spheres are present, the compound is neutral. In contrast, when m=1, only monofunctional coordination spheres are present and the Pt moiety has a formal charge of 2+ which must be counterbalanced by one or more counter-anions having a net charge of 2−.

In spite of the foregoing, there remains a long-felt need in the art to develop a cancer therapeutic agent which provides platinum complexes having improved solubility together with well established chemical reproducibility and characterization.

OBJECTS AND SUMMARY OF THE INVENTION

As discussed supra, mono(platinum) and bis(platinum) complexes and the use thereof as cancer therapeutic agents is known in the art. In contrast, the present invention describes the synthesis of bis(platinum) (IV) complexes wherein the platinum atoms are linked by a diamine bridging agent, which complexes are water soluble. Because of the water solubility of the platinum atoms, administration of these complexes provides for enhanced mediation of cytotoxicity.

In its broadest aspect, it is an object of this invention to provide bis(platinum) (IV) complexes wherein two platinum coordination spheres are linked by a diamine bridging agent, and wherein the platinum complexes are water soluble.

It is a further object of the invention to provide pharmaceutical compositions containing water soluble bis(platinum) (IV) complexes wherein the platinum coordination spheres are linked by a diamine bridging agent.

It is another object of the invention to provide methods for synthesizing water soluble bis(platinum) (IV) complexes wherein the platinum coordination spheres are linked by a diamine bridging agent.

It is a specific object of the invention to provide bis(platinum) (IV) complexes the formula (I):

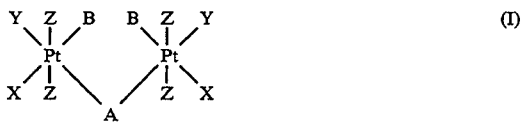

wherein Z is —OCO—R, —OC(O)OR or —OSO$_2$—R, wherein R is H, linear or branched $C_1$-$C_8$ alkyl, $C_3$-$C_6$ cycloalkyl, phenyl, substituted phenyl, or $C_7$-$C_{10}$ aralkyl; B is an inert ligand such as ammonia, a primary, secondary or tertiary amine or a nitrogen-heterocyclic ligand; A is a bridging diamine; and X and Y, which are the same or different, are an anionic leaving ligand such as halide, sulfate, nitrate, hydroxy, carboxylate, substituted carboxylate or pseudohalogen, or X and Y taken together represent a divalent chelating group such as a dicarboxylate or a glycolate.

It is another specific object of the invention to provide pharmaceutical compositions containing the bis(platinum) (IV) complex of formula (I).

It is a further object of the invention to provide a method of use of bis(platinum) (IV) complexes of formula (I) for therapeutic use, e.g., for treatment of tumors or parasitic conditions.

It is still another specific object of the invention to provide a method for synthesizing bis(platinum) (IV) complexes of the formula (I).

The subject bis(platinum) (IV) complexes, by virtue of their water solubility, provide for enhanced cytotoxic activity relative to currently available bis(platinum) (IV) complexes.

DESCRIPTION OF THE PREFERRED EMBODIMENTS OF THE INVENTION

The present invention provides a novel class of bis(platinum) (IV) complexes which exhibit enhanced cytotoxic activity as compared to currently available platinum complexes. The bis(platinum) (IV) complexes of the present invention are water soluble. In particular, such bis(platinum) (IV) complexes comprise the formula (I):

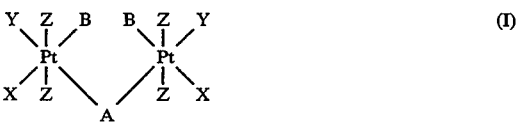

wherein Z is —OCO—R, —OC(O)OR or —OSO$_2$—R, R is H, linear or branched $C_1$-$C_8$ alkyl, $C_3$-$C_6$ cycloalkyl, phenyl, substituted phenyl, or $C_7$-$C_{10}$ aralkyl; B is an inert ligand such as ammonia, a primary, secondary or tertiary amine and a nitrogen-heterocyclic ligand; A is a bridging diamine; and X and Y, which are the same or different, are an anionic leaving ligand such as halide, sulfate, nitrate, hydroxy, carboxylate, substituted carboxylate or pseudohalogen, or X and Y taken together represent a divalent chelating group such as a dicarboxylate or a glycolate.

Suitable Z groups include —OCO—R, —OC(O)OR and —OSO$_2$—R; wherein R is linear or branched $C_1$-$C_8$ preferably, methyl, ethyl, n-propyl, isopropyl, n-butyl, sec-butyl, tert-butyl, n-pentyl, n-hexyl, n-octyl, and the like. Suitable Z groups also include —OCO—R, —OC(O)OR and —OSO$_2$—R; wherein R is $C_3$-$C_6$ cycloalkyl, preferably, cyclopropyl, cyclobutyl, cyclopentyl, cyclohexyl, and the like. Suitable Z groups further include —OCO—R, —OC(O)OR and —OSO₂—R; wherein R is substituted phenyl, preferably, ortho, meta and para tolyl, phenyl rings substituted with one or two halogens such as chloride, bromide or fluoride, and the like, or mono and dimethoxy substituted phenyl. Suitable Z groups also include —OCO—R, —OC(O)OR and —OSO₂—R; wherein R is $C_7$–$C_{10}$ aralkyl, preferably, phenylmethyl, phenylethyl, phenylpropyl, and the like.

Suitable inert ligands B include: (a) primary amines such as alkyl amines of the formula $NH_2R_1$; wherein $R_1$ is linear or branched $C_1$–$C_8$ alkyl, preferably, methyl, ethyl, n-propyl, isopropyl, n-butyl, sec-butyl, tert-butyl, n-pentyl, n-hexyl, n-octyl, and the like; and wherein $R_1$ is $C_3$–$C_6$ cycloalkyl, preferably, cyclopropyl, cyclobutyl, cyclopentyl, cyclohexyl, and the like, (b) secondary amines such as alkyl amines of the formula $NH(R_1)_2$; wherein $R_1$ is linear or branched $C_1$–$C_8$ alkyl, preferably, methyl, ethyl, n-propyl, isopropyl, n-butyl, sec-butyl, tert-butyl, n.-pentyl, n-hexyl, n-octyl, and the like; and wherein $R_1$ is $C_3$–$C_6$ cycloalkyl, preferably, cyclopropyl, cyclobutyl, cyclopentyl, cyclohexyl, and the like, and (c) nitrogen-heterocyclic ligands such as saturated or unsaturated heterocyclic rings, preferably, pyridine, quinoline, isoquinoline, thiazole, imidazole, substituted pyridine, substituted quinoline or isoquinoline, pipeddine, pyrrolidine, morpholine N-alkyl, N-acyl-piperazine, and the like.

The bridging diamine A preferably has the formula:

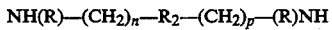

NH(R)—(CH₂)ₙ—R₂—(CH₂)ₚ—(R)NH wherein R is H, linear or branched $C_1$–$C_8$ alkyl, $C_3$–$C_6$ cycloalkyl, phenyl, substituted phenyl, or $C_7$–$C_{10}$ aralkyl; n and p, which are the same or different, are an integer between 1 and 4; and R2 is —CH(OH)—, —CH₂—, —CO—, —OC(O)O—, —SO₂—, —OS(O₂)O— or —OP(O)(OH)O—. Bridging diamine A more preferably includes straight chain diamines having the formula:

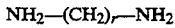

NH₂—(CH₂)ᵣ—NH₂ wherein r is an integer from 2 to 9.

Suitable anionic leaving ligands X and Y include carboxylate groups, preferably, acetate, propionate, butarrate,, chloroacetate, hydroxyacetate, benzoate, and the like; and chelating dicarboxylate groups, preferably, oxalate, malonate, substituted malonate, succinate, glutarate, phthalate, and the like. Preferable substituted malonate groups include compounds of the formula:

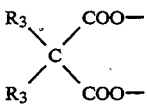

wherein R₃, which are the same or different, are hydrogen (with the provision that only one R₃ is hydrogen); linear or branched $C_1$–$C_8$ alkyl, preferably, methyl, ethyl, n-propyl, iso-propyl, n-butyl, sec-butyl, tert-butyl, n-pentyl, n-hexyl, n-octyl, and the like; or both the groups R₃ taken together represent a $C_3$–$C_6$ cycloalkyl such as cyclopropyl, cyclobutyl, cyclopentyl, cyclohexyl, and the like, or —CH₂OH.

Examples of anionic ligands X and Y also include halides, such as $Cl^-$, $Br^-$, $I^-$, and the like and pseudohalides. Pseudohalides are substances containing two or more electronegative atoms, which in the free state, resemble the halogens.

These pseudohalogens give rise to anions which resemble the halide ions in behaviour. Pseudohalides (wherein the definition for "pseudohalide" as set forth on page 560 of "Advanced Inorganic Chemistry" by Cotton and Wilkinson, insert date, and PCT/US87/01738 page 5, lines 20–26, is incorporated by reference herein) suitable for use in the bis(platinum) (IV) complexes of the present invention include $SCN^-$, $CN^-$, $OCN^-$, $NO_3^-$, carboxylates, monovalent anions such as $PF_6^-$, $BF_4^-$, anionic ligands, divalent anions such as $SO_4^{-2}$, and the like.

The water soluble bis(platinum) (IV) complexes of the present invention include the following compounds:

μ-(1,5-pentanediamine-N,N')bis[cis, trans-amminedichlorodiacetoxy-platinum(IV)];

μ-(1,5-pentanediamine-N,N')bis[cis, trans-amminedichlorodibutyryloxoplatinum(IV)];

μ-(1,5-pentanediamine-N,N')bis[cis, trans-amminedichlorodi(trifluoroacetoxy)platinum(IV)];

μ-(1,4-butanediamine-N,N')bis[cis, trans-amminedichlorodiacetoxy-platinum(IV)];

μ-(1,6-hexanediamine-N,N')bis[cis, trans-amminedichlorodiacetoxy-platinum(IV)];

μ-(1,6-hexanediamine-N,N')bis[cis, trans-amminedichlorodipropionyloxy-platinum(IV)];

μ-(1,4-butanediamine-N,N')bis[cis, trans-amminedichlorodipropionyloxy-platinum(IV)];

μ-(1,5-pentanediamine-N,N')bis[cis, trans-amminedichlorodipropionyloxy-platinum(IV)];

μ-(1,6-hexanediamine-N,N')bis[cis, trans-amminedichlorodibutyryloxy-platinum(IV)];

μ-(1,4-butanediamine-N,N')bis[cis, trans-amminedichlorodibutyryloxy-platinum(IV)];

μ-(1,5-pentanediamine-N,N')bis[cis, trans-ammine(1,1-cyclobutanedicarboxylato(2-) O,O')-diacetoxy-platinum(IV)];

μ-(1,5-pentanediamine-N,N')bis[cis, trans-ammine(1,1-cyclobutanedicarboxylato(2-) O,O')dipropionyloxy-platinum(IV)];

μ-(1,5-pentanediamine-N,N')bis[cis, trans-ammine(1,1-cyclobutanedicarboxylato(2-) O,O')-dibutyryloxy-platinum(IV)];

μ-(1,4-butanediamine-N,N')bis[cis, trans-ammine(-propanedioato(2-)-O,O')diacetoxy -platinum(IV)];

μ-(1,4-butanediamine-N,N')bis[cis, trans-ammine(-propanedioato(2-)-O,O')dibutyryl oxy-platinum(IV)];

μ-(1,6-hexanediamine-N,N')bis[cis, trans-ammine(-propanedioato(2-)-O,O')dibutyryl oxyplatinum-(IV)];

μ-(1,6-hexanediamine-N,N')bis[cis, trans-ammine(-propanedioato(2-)-O,O')dipropionyloxyplatinum-(IV)];

μ-(3-hydroxy-1,5-pentanediamine-N,N')bis[cis, trans-ammine(1,1-cyclobutanedicarboxylato (2-)-O,O')-diacetoxy-platinum(IV)];

μ-(3-hydroxy-1,5-pentanediamine-N,N')bis[cis, trans-ammine(propanedioato(2-) -O,O')diacetoxy-platinum(IV)];

μ-(3-hydroxy-1,5-pentanediamine-N,N')bis[cis, trans-ammine(1-ethylpropanedioato (2-)O,O')diacetoxy-platinum(IV)];

μ-(3-hydroxy-1,5-pentanediamine-N,N')bis[cis, trans-ammine (1,1-cyclobutanedicar-boxylato(2-)-O,O')-dibutyryloxy-platinum(IV)];

μ-(1,5-pentanediamine-N,N')bis[cis, trans-amminedichloroformiloxyhydroxoplatinum(IV)];

μ-(1,5-pentanediamine-N,N')bis[cis, trans-ammine(propanedioato(2-)-O,O')diacetoxy-platinum(IV)];

μ-(1,5-pentanediamine-N,N')bis[cis, trans-ammine(propanedioato(2-)-O,O')dipropionyloxy-platinum(IV)]; and μ-(1,5-pentanediamine-N,N')bis[cis, trans-ammine(propanedioato(2-)-O,O')dibutyryloxy-platinum(IV)].

The water soluble bis(platinum) (IV) complexes of the present invention will preferably be synthesized by the following procedure. The preparation of the bis(platinum) (IV) compounds of the present invention can be accomplished by reacting a compound of formula II:

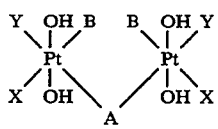

wherein X, Y, A and B are as previously described above, with an appropriate acylating or sulfonilating agent in a suitable solvent, such as dimethylformamide, N-methylpyrrolidone, N-methylacetamide, mixtures thereof, and the like, with the acylating agent used as a solvent.

Suitable acylating agents include anhydrides of the formula:

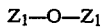

wherein $Z_1$ is —CO—R or —C(O)OR; acyl or sulfonyl chlorides of the formula:

wherein $Z_2$ is a group selected among —CO—R, —C(O)OR and —SO$_2$R, wherein R is as previously defined above. The platinum complexes of formula II can be prepared by following the procedures reported in PCT WO 88/00947.

The bis(platinum) (IV) complexes of the present invention are intended for use in pharmaceutical compositions. Given the water solubility of the bis(platinum) (IV) complexes, the complexes of the present invention should exhibit greater cytotoxic activity than currently available platinum complexes. The relatively high solubility in water is most advantageous for antitumor agents, since it permits administration in a concentrated solution, i.e., in a small volume of injection or infusion vehicle. This can be particularly advantageous where it is desirable to administer the antitumor agent in the vicinity of a tumor location, e.g., by intravenous or intraarterial administration over a relatively short period of time for maximum impact at the tumor site. Further, the ready solubility in water of the bis(platinum) (IV) complexes of the present invention is advantageous for oral administration. Depending on the stability, the potency, the bioavailability and the side effects of a particular compound, and the like, oral administration may be indicated.

The subject complexes are useful for treatment of the identical diseases and conditions for which cisplatin is used. This includes the treatment of tumors, radiation sensitization or potentiation (Douple et al, *Cisplatin Current Status and Developments*, Eds. A. W. Prestayk et al, Academic Press, 125 (1980); Douple et al, *Platinum Metals Res.*, (1985), 29, 118), and treatment of parasitic diseases such as sleeping sickness (Farrell et al, *Biochem. Pharmacol.*, (1984), 33, 961). The complexes of the present invention will preferably be administered at the same dosage levels of cisplatin, while taking into account the LD$_{50}$ value of the particular bis(platinum) (IV) complex.

Generally, the bis(platinum) (IV) complex will be combined with a pharmaceutically acceptable carrier. For example, the complex and carrier may be formulated for parenteral or oral administration by methods well known in the art. For instance, see *Remington's Pharmaceutical Sciences* for suitable pharmaceutically acceptable carriers and formulation methods.

Given the structure and water: solubility of the bis(platinum) (IV) complexes of the present invention, these complexes would be useful in the treatment of ovarian, head and neck, and small cell lung cancers, parasitic disorders and other conditions wherein platinum complexes find current therapeutic usage. The therapeutic efficacy of a particular bis(platinum) (IV) complex will be evaluated by standard methods. For example, the cytotoxic activity of a particular bis(platinum) (IV) complex may be evaluated in vitro based on its cytotoxicity against L1210 cancer cells, P388 cancer cells, or L1210 or P388 cancer cells resistant to cisplatin. The L1210 assay, in particular, is an accepted method for screening platinum complexes for therapeutic activity.

Those bis(platinum) (IV) complexes which exhibit cytotoxic activity, e.g., against L1210 cells, will then be tested in animals, e.g., nude mice containing implanted human tumors. Those bis(platinum) (IV) complexes which exhibit in vivo activity without substantial adverse effects (e.g., nephrotoxicity) would be then tested clinically in humans.

In order to fully illustrate the present invention and the advantages thereof, the following specific examples are given, it being understood that these examples are intended only to be illustrative without serving as a limitation on the scope of the present invention.

The preparation of a bis(platinum) (IV) compound of the present invention is shown schematically supra.. The actual experimental procedures used to synthesize the following compounds of the present invention are described as follows:

EXAMPLE 1

Preparation of μ-(1,5-pentanediamine-N,N')bis[cis, transamminedichlorodihydro-platinum(IV)]

1.34 g (2 mmoles) of μ-(1,5-pentanediamine-N,N')bis[cis-amminedichloro-platinum(II)] is suspended in 20 ml of water and heated to 60° C. H$_2$O$_2$ (30 % m/v -40 ml) is added and the resultant solution is heated at 60° C. for one hour. The yellow solution is concentrated in a rotary evaporator to 5 ml and acetone added to precipitate the product as a light yellow solid. The solid is filtered, washed with acetone and ether and dried in vacuo.

Yield 1.34 g (92 %). Elemental analysis (Found/Calculated for C$_5$H$_{24}$N$_4$Cl$_4$Pt$_2$): C, 8.09/8.16; H, 3.44/3.29; N, 7.29/7.61; Cl, 18.38/19.26; Pt, 50.67/52.99. Calculated for C$_5$H$_{24}$N$_4$O$_4$Cl$_4$Pt$_2$×H$_2$O$_2$: C, 7.80; H, 3.40; N, 7.27; Cl, 18.41; Pt, 50.65. I.R. (cm$^{-1}$, KBr disks): 3538ν$_{(OH)}$ 3213ν$_{(NH)}$ 549ν$_{(Pt-O)}$ $^{195}$Pt-NMR (H$_2$O/H$_2$O$_2$), reference K$_2$PtCl$_4$: +855 ppm.

EXAMPLE 2

Preparation of μ-(1,5-pentanediamine-N,N')bis[cis, transammine(propanedioato(2-)O,O')dihydroxo-platinum(IV)]

365 mg (0.5 mmoles) of μ-(1,5-pentanediamine-N,N')bis[ammine(propanedioato(2-)O,O')platinum(II)] is dissolved in 5 ml of water at 60° C. and H$_2$O$_2$ (30 % m/v, 10 ml) is added. The colorless solution is heated at 60° C. for one hour and evaporated to dryness. The residue is taken up in MeOH and diluted with ether. The precipitated solid is collected, washed with ether and dried.

Yield 285 mg (71 %). Elemental analysis (Found/Calculated for C$_{11}$H$_{28}$N$_4$O$_{12}$Pt$_2$×2H$_2$O): C, 15.80/15.83; H, 4.16/3.86; N, 6.09/6.71. I.R. (cm$^{-1}$, KBr disks): 3420$\nu_{(OH)}$ 3320$\nu_{(NH)}$ 1635$\nu_{(C=O)}$ 1370$\nu_{(C-O)}$ 560$\nu_{(Pt-O)}$ $^{195}$Pt-NMR (H$_2$O/H$_2$O$_2$), reference K$_2$PtCl$_4$: +1636 ppm.

$^1$H-NMR (D$_2$O):1.45–1.60 (m,2H, CH$_2$ diamine); 1.65–1.80 (m,4H,CH$_2$ diamine); 2.7–2.9 (4H, m,CH$_2$N) (protons on malonate ring undergo fast exchange with D$_2$O and are not visible).

EXAMPLE 3

Following the procedure outlined in Example 2, the following complexes were synthesized:
- μ-(1,5-pentanediamine-N,N')bis[cis, trans-ammine(1,1-cyclobutanedicarboxylato(2-) -O,O')-dihydroxo-platinum(IV)];
- μ-(1,5-pentanediamine-N,N')bis[cis, trans-ammine(1-ethylpropanedioato(2-)-O,O')dihydroxoplatinum(IV)];
- μ-(1,4-butanediamine-N,N')bis[cis, trans-ammine(1,1-cyclobutanedicarboxylato(2-) -O,O')dihydroxo-platinum(IV)];
- μ-(1,4-butanediamine-N,N')bis[cis, trans-ammine(-propanedioato(2-) -O,O')dihydroxoplatinum(IV)];
- μ-(1,4-butanediamine-N,N')bis[cis, trans-ammine(1-ethylpropanedioato(2-)-O,O')-dihydroxoplatinum(IV)];
- μ-(1,6-hexanediamine-N,N')bis[cis, trans-ammine(1,1-cyclobutanedicarboxylato(2-) -O,O')dihydroxo-platinum(IV)];
- μ-(1,6-hexanediamine-N,N')bis[cis, trans-ammine(-propanedioato(2-)-O,O')dihydroxoplatinum(IV)];
- μ-(1,6-hexanediamine-N,N')bis[cis, trans-ammine(1-ethylpropanedioato(2-)-O,O')-dihydroxoplatinum(IV)];
- μ-(3-hydroxy-1,5-pentanediamine-N,N')bis[cis, trans-ammine(1,1-cyclobutanedicarboxylato(2) -O,O')-dihydroxo-platinum(IV)];
- μ-(3-hydroxy-1,5-pentanediamine-N,N')bis[cis, trans-ammine(propanedioato(2-)-O,O')dihydro xo-platinum(IV)]; and
- μ-(3-hydroxy-1,5-pentanediamine-N,N')bis[cis, trans-ammine(1-ethylpropanedioato(2-) -O,O')dihydroxo-platinum(IV)].

EXAMPLE 4

Preparation of μ-(1,5-pentanediamine-N,N')bis[cis, trans-amminedichlorodiacetoxy-platinum(IV)]

368 mg (0.5 mmoles) of μ-(1,5-pentanediamine-N,N')bis[cis, trans-amminedichlorodihydroxo-platinum(IV)] is suspended in 5 ml of acetic anhydride and stirred at room temperature for 1 week. The solution is filtered to remove a small amount of insoluble material and diluted with ether. The light yellow solid thus obtained is filtered, resuspended in ether and filtered again, washed with ether and dried under vacuum.

Yield 295 mg (65 %). Elemental analysis (Found/Calculated): C, 17.27/17.26; H, 3.82/3.57; N, 5.95/6.19; Cl, 14.99/15.68; Pt, 41.71/43.14. I.R. (cm$^{-1}$, KBr disks): 3437$\nu_{(OH)}$ 3210$\nu_{(NH)}$ 1621$\nu_{C=O}$ 1363, 1289$\nu_{C-O}$ $^{195}$Pt-NMR (Ac$_2$O), reference K$_2$PtCl$_4$: +1130 ppm.

$^1$H-NMR (MeOD):1.35–1.60 (m,2H,CH$_2$ diamine); 1.60–1.85 (m,4H,CH$_2$ diamine); 2.08 (s,12H, CH$_3$)2.70–3.0 (m,4H, CH$_2$N diamine). Mass spectrometer evaluation: fab/mf: m/z 904.

By reacting μ-(1,5-pentanediamine-N,N')bis[cis, trans-amminedichlorodihydroxoplatinum(IV)] with acetyl chloride (6eq) in DMF the same compound is obtained in a lower yield (24%).

EXAMPLE 5

Preparation of μ-(1,5-pentanediamine-N,N')bis[cis, trans-amminedichlorodibutyryloxoplatinum(IV)]

37 mg of μ-(1,5-pentanediamine-N,N')bis[cis, trans-amminedichlorodihydroxoplatinum(IV)] is suspended in a mixture of butyric anhydride (0.5 ml) and DMF (0.5 ml) and stirred at room temperature for 4 days. The light yellow solution obtained is diluted with ether to separate a solid which is filtered, resuspended in diethyl ether and again filtered. This procedure was repeated several times to yield a light yellow solid.

$^{195}$Pt-NMR(DMF-(BuCO)$_2$O), reference K$_2$PtCl$_4$: +1174 ppm.

$^1$H-NMR (MeOD): 0.87–1.05 (t,12H,CH$_3$); 1.35–1.80 (m,CH$_2$ diamine; m, CH$_2$ butyryl, 14H); 2.25–2.40 (t,8H,CH$_2$C=O); 2.75–2.90 (m,4H,CH$_2$N).

EXAMPLE 6

Preparation of μ-(1,5.-pentanediamine,N,N')bis[cis, trans-amminedichlorodi(trifluoroacetoxy)-platinum-(IV)]

73 mg (0.1 mmoles) of μ-(1,5-pentanediamine-N,N')bis[cis, trans-amminedichlorodihydroxo-platinum(IV)] is suspended in 2 ml of acetonitrile and 1 ml of trifluoroacetic anhydride is added. The solution is stirred for 15 minutes and evaporated to dryness to yield a glassy residue which is treated with an ether/hexane mixture. The solid is filtered, washed with hexane and dried.

Yield 83 mg (74%). Elemental analysis (Found/Calculated for C$_{13}$H$_{20}$Cl$_4$F$_{12}$N$_4$O$_8$Pt$_2$): C, 14.65/13.94; H 1.95/1.80; N, 5.06/5.00; Cl, 12.25/12.66; F, 19.13/20.35; Pt, 34.48/34.83. I.R. (cm$^{-1}$, KBr disks): 3445$\nu_{(OH)}$ 3194$\nu_{(NH)}$ 1724–1703$\nu_{(C=O)}$ 1386, 1217$\nu_{(C-O)}$ 1166$\nu_{C-F}$ $^{195}$Pt-NMR (MeOH) reference K$_2$PtCl$_4$: +1095 ppm.

EXAMPLE 7

Following the procedure reported in Examples 4, 5 and 6, and reacting the platinum (II) dichloro derivatives described in PCT WO 88/0094 the following compounds were obtained:
- μ-(1,4-butanediamine-N,N')bis[cis, trans-amminedichlorodiacetoxy-platinum(IV)];
- μ-(1,6-hexanediamine-N,N')bis[cis, trans-amminedichlorodiacetoxy-platinum(IV)];

μ-(1,6-hexanediamine-N,N')bis[cis, trans-amminedichlorodipropionyloxy-platinum(IV)];
μ-(1,4-butanediamine-N,N')bis[cis, trans-amminedichlorodipropionyloxy-platinum(IV)];
μ-(1,5-pentanediamine-N,N')bis[cis, trans-amminedichlorodipropionyloxy-platinum(IV)];
μ-(1,6-hexanediamine-N,N')bis[cis, trans-amminedichlorodibutyryloxy-platinum(IV)]; and
μ-(1,4-butanediamine-N,N')bis[cis, trans-amminedichlorodibutyryloxy-platinum(IV)].

EXAMPLE 8

Following the procedures reported in Examples 4, 5 and 6 and using the platinum (IV) complexes of Example 3 as starting material, the following compounds were obtained by reaction with the appropriate anhydrides::

μ-(1,5-pentanediamine-N,N') bis[cis, trans-ammine(1,1-cyclobutanedicarboxylato(2-) -O,O')-diacetoxy-platinum(IV)];

μ-(1,5-pentanediamine-N,N')bis[cis, trans-ammine(1,1-cyclobutanedicarboxylato(2-) -O,O')-dipropionyloxy-platinum(IV)];

μ-(1,5-pentanediamine-N,N')bis[cis, trans-ammine(1,1-cyclobutanedicarboxylato(2-) -O,O')-dibutyryloxy-platinum(IV)];

μ-(1,5-pentanediamine-N,N')bis[cis, trans-ammine(1-ethylpropanedioato(2-) -O,O')diacetoxyplatinum(IV)];

μ-(1,5-pentanediamine-N,N')bis[cis, trans-ammine(1-ethylpropanedioato(2-) -O,O')dipropionyloxy-platinum(IV)];

μ-(1,5-pentanediamine-N,N')bis [cis, trans-ammine(1-ethylpropanedioato(2-) -O,O')dibutyryloxy-platinum(IV)];

μ-(1,4-butanediamine-N,N')bis[cis, trans-ammine(1,1-cyclobutanedicarboxylato(2-) -O,O')diacetoxy-platinum(IV)];

μ-(1,4-butanediamine-N,N')bis[cis, trans-ammine(1,1-cyclobutanedicarboxylato(2-) -O,O')dipropionyloxy-platinum(IV)];

μ-(1,4-butanediamine-N,N')bis[cis, trans-ammine(1,1-cyclobutanedicarboxylato(2-) -O,O')dibutyryloxy-platinum(IV)];

μ-(1,4-butanediamine-N,N')bis[cis, trans-ammine(-propanedioato(2-) -O,O')diacetoxyplatinum(IV)];

μ-(1,4-butanediamine-N,N')bis[cis, trans-ammine(-propanedioato(2-) -O,O')dibutyryloxyplatinum(IV)];

μ-(1,4-butanediamine-N,N')bis[cis, trans-ammine(1-ethylpropanedioato(2-) -O,O')di-acetoxyplatinum(IV)];

μ-(1,4-butanediamine-N,N')bis[cis, trans-ammine(1-ethylpropanedioato(2-) -O,O')dipropionyloxy-platinum(IV)];

μ-(1,4-butanediamine-N,N')bis[cis, trans-ammine(1,1-cyclobutanedicarboxylato(2-) -O,O')dibutyryloxy-platinum(IV)];

μ-(1,6-hexanediamine-N,N')bis[cis, trans-ammine(1,1-cyclobutanedicarboxylato(2-) -O,O') diacetoxy-platinum(IV)];

μ-(1,6-hexanediamine-N,N')bis[cis, trans-ammine(1,1-cyclobutanedicarboxylato(2-) -O,O')dipropionyloxy-platinum(IV)];

μ-(1,6-hexanediamine-N,N')bis[cis, trans-ammine(1,1-cyclobutanedicarboxylato(2-) -O,O')dibutyryloxy-platinum(IV)];

μ-(1,6-hexanediamine-N,N')bis[cis, trans-ammine(-propanedioato(2-)-O,O')diacetoxyplatinum(IV)];

μ-(1,6-hexanediamine-N,N')bis[cis, trans-ammine(-propanedioato(2-)-O,O')dibutyryloxyplatinum(IV)];

μ-(1,6-hexanediamine-N,N')bis[cis, trans-ammine(-propanedioato(2-)-O,O')di-propionyloxyplatinum(IV)];

μ-(1,6-hexanediamine-N,N')bis[cis, trans-ammine(1-ethylpropanedioato(2-)-O,O')di-acetoxyplatinum(IV)];

μ-(1,6-hexanediamine-N,N')bis[cis, trans-ammine(1-ethylpropanedioato(2-) -O,O')dipropionyloxy-platinum(IV)];

μ-(1,6-hexanediamine-N,N')bis[cis, trans-ammine(1-ethylpropanedioato(2-)-O,O') dibutyryloxy-platinum(IV)];

μ-(3-hydroxy-1,5-pentanediamine-N,N')bis[cis, trans-ammine(1,1-cyclobutanedicarboxylato (2-)-O,O')-diacetoxy-platinum(IV)];

μ-(3-hydroxy-1,5-pentanediamine-N,N')bis[cis, trans-ammine(propanedioato(2-) -O,O')diacetoxy-platinum(IV)];

μ-(3-hydroxy-1,5-pentanediamine-N,N')bis[cis, trans-ammine(1-ethylpropanedioato(2-) -O,O')-diacetoxy-platinum(IV)];

μ-(3-hydroxy-1,5-pentanediamine-N,N')bis[cis, trans-ammine(1,1-cyclobutanedicarboxylato (2-)-O,O')-dibutyryloxy-platinum(IV)];

μ-(3-hydroxy-1,5-pentanediamine-N,N')bis[cis, trans-ammine(Propanedioato(2-) -O,O')dipropionyloxy-platinum(IV)]; and μ-(3-hydroxy-1,5-pentanediamine-N,N')bis[cis, trans-ammine(propanedioato(2-) -O,O')dibutyryloxy-platinum(IV)].

EXAMPLE 9

Preparation of μ-(1,5-pentanediamine-N,N')bis[cis, trans-amminedichloroformiloxyhydroxoplatinum(IV)]

73 mg (0.1 mmoles) of μ-(1,5-pentanediamine-N,N')bis[cis, trans-amminedichlorodihydroxoplatinum(II)] is dissolved in 2 ml of formic acid 99% and heated at 50° C. for one hour.

The solution is evaporated to dryness, the residue taken up in methanol and diluted with ether. The solid is collected, washed with ether and dried.

Yield 42 mg.

$^1$H-NMR (MeOD): 1.38–1.58 (m,2H,CH$_2$ aliamine); 1.65–1.9 (m,4H, CH$_2$ diamine); 2.65–2.9 (m,4H,CH$_2$N); 8.08 (t,J$_{Pt-H}$32.5 Hz,2H, HCO).

EXAMPLE 10

Preparation of μ-(1,5-pentanediamine-N,N')bis[cis, trans-ammine(propanedioato(2-) -O,O'diacetoxy-platinum(IV)]

400 mg (0.5 mmoles) of μ-(1,5-pentanediamine-N,N')bis[cis, trans-ammine(propanedioato(2-)-O,O')-dihydroxoplatinum(IV)] is dissolved in 10 ml of water at room temperature and 50 ml of acetic anhydride are added. The mixture is stirred for 1 hour and diluted with ether. The solvents are decanted, the residue stirred with ether and the solvents decanted again. This process is repeated several times until a white solid is obtained. The product is filtered, washed with ether and dried.

Yield 358 mg (74%).

$^1$H-NMR (D$_2$O): 1.40–1.60 (m,2H,CH$_2$ diamine); 1.65–1.82 (m,4H, CH$_2$ diamine); 2.15 (s,12H,acetyl); 2.7–2.85 (4H,m,CH$_2$N); 3.85 (bs. CH$_2$ on malonate ring, partially exchanged with D$_2$O).

EXAMPLE 11

Following the procedure outlined in Example 10, the following complexes were synthesized:

μ-(1,5-pentanediamine-N,N')bis[cis, trans-ammine(-propanedioato(2-) -O,O')diacetoxy-platinum(IV)];

μ-(1,5-pentanediamine-N,N')bis[cis, trans-ammine(-propanedioato(2-) -O,O')dipropionyloxy-platinum-(IV)]; and μ-(1,5-pentanediamine-N,N')bis[cis, trans-ammine(-propanedioato(2-) -O,O')dibutyryloxy-platinum-(IV)].

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

We claim:

1. A bis(platinum) (IV) complex of the formula (I):

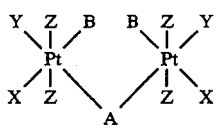

wherein Z is —OCO—R, —OC(O)OR or —OSO$_2$—R, R is H, linear or branched C$_1$–C$_8$ alkyl, C$_3$–C$_6$ cycloalkyl, phenyl, substituted phenyl, or C$_7$–C$_{10}$ aralkyl; B is an inert ligand, wherein said inert ligand is ammonia, a primary, secondary or tertiary amine, or a nitrogen-heterocyclic ligand; A is a bridging diamine; and X and Y, which are the same or different, are an anionic leaving ligand, wherein said leaving ligand is a halide, sulfate, nitrate, hydroxy, carboxylate, substituted carboxylate or pseudohalogen, or X and Y taken together represent a divalent chelating group.

2. The bis(platinum) (IV) complex of claim 1, wherein Z is —OCO—R, —OC(O)OR or —OSO$_2$—R and R is linear or branched C$_1$–C$_8$ alkyl.

3. The bis(platinum) (IV) complex of claim 1, wherein Z is —OCO—R, —OC(O)OR or —OSO$_2$—R and R is C$_3$–C$_6$ cycloalkyl.

4. The bis(platinum) (IV) complex of claim 1, wherein Z is —OCO—R, —OC(O)OR or —OSO$_2$—R and R is ortho, meta or para tolyl, phenyl ring substituted with one or two halogens, or mono or dimethoxy substituted phenyl.

5. The bis(platinum) (IV) complex of claim 4, wherein said substituted phenyl is a phenyl ring substituted with one or two of chloride, bromide and fluoride.

6. The bis(platinum) (IV) complex of claim 1, wherein Z is —OCO—R, —OC(O)OR or —OSO$_2$—R and R is C$_7$–C$_{10}$ aralkyl.

7. The bis(platinum) (IV) complex of claim 1, wherein inert ligand B is a primary alkyl amine of the formula NH$_2$R$_1$ and R$_1$ is linear or branched C$_1$–C$_8$ alkyl.

8. The bis(platinum) (IV) complex of claim 1, wherein inert ligand B is a primary alkyl amine of the formula NH$_2$R$_1$ and R$_1$ is C$_3$–C$_6$ cycloalkyl.

9. The bis(platinum) (IV) complex of claim 1, wherein inert ligand B is a secondary alkyl amine of the formula NH(R$_1$)$_2$ and R$_1$ is linear or branched C$_1$–C$_8$ alkyl.

10. The bis(platinum) (IV) complex of claim 1, wherein inert ligand B is a secondary alkyl amine of the formula NH(R$_1$)$_2$ and R$_1$ is C$_3$–C$_6$ cycloalkyl.

11. The bis(platinum) (IV) complex of claim 1, wherein said nitrogen-heterocyclic ligand is a saturated or unsaturated heterocyclic ring, wherein said ring is pyridine, quinoline, isoquinoline, imidazole, piperidine, pyrrolidine, morpholine N-alkyl or N-acyl-piperazine.

12. The bis(platinum) (IV) complex of claim 1, wherein said bridging diamine A has the formula:

NH(R)—(CH$_2$)$_n$—R$_2$—(CH$_2$)$_p$—(R)NH wherein R is H, linear or branched C$_1$–C$_8$ alkyl, C$_3$–C$_6$ cycloalkyl, phenyl, substituted phenyl, or C$_7$–C$_{10}$ aralkyl; n and p, which are the same or different, are an integer between 1 and 4; and R$_2$ is —CH(OH)—, —CH$_2$—, —CO—, —OC(O)O—, —SO$_2$—, —OS(O$_2$-)O— or —OP(O)(OH)O—.

13. The bis(platinum) (IV) complex of claim 1, wherein said bridging diamine A is a straight chain diamine having the formula:

NH$_2$—(CH$_2$)$_r$—NH$_2$ wherein r is an integer from 2 to 9.

14. The bis(platinum) (IV) complex of claim 1, wherein said anionic leaving ligands X and Y taken together represent a dicarboxylate or a glycolate divalent chelating group.

15. The bis(platinum) (IV) complex of claim 1, wherein said anionic leaving ligans X and Y are acetate, propionate, butarrate, chloroacetate, hydroxyacetate or benzoate.

16. The bis(platinum) (IV) complex of claim 1, wherein said anionic leaving ligands X and Y taken together are chelating dicarboxylates.

17. The bis(platinum) (IV) complex of claim 16, wherein said substituted malonate is a compound of the formula:

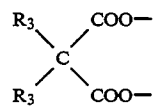

wherein R$_3$, which are the same or different, are hydrogen (with the provision that only one R$_3$ is hydrogen); linear or branched C$_1$–C$_8$ alkyl; or both the groups R$_3$ taken together represent a C$_3$–C$_6$ cycloalkyl or —CH$_2$OH.

18. The bis(platinum) (IV) complex of claim 1, wherein the pseudohalogen is a carboxylate, monovalent anion, anionic ligand or divalent anion.

19. A method for making the bis(platinum) (IV) complex of claim 1, comprising:

reacting a compound of formula II:

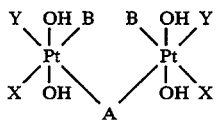

wherein B is an inert ligand, Wherein said inert ligand is ammonia, a primary, secondary or tertiary amine or a nitrogen-heterocyclic ligand; A is a bridging diamine; and X and Y, which are the same or different, are an anionic leaving ligand, wherein said leaving ligand is a halide, sulfate, nitrate, hydroxy, carboxylate, substituted carboxylate or pseudohalogen, or X and Y taken together represent a divalent chelating group, with an appropriate acylating or sulfonilating agent in a suitable solvent of dimethylformamide, N-methylpyrrolidone, N-methylacetamide or mixtures thereof, wherein the acylating agent is a solvent.

20. The method of claim 19, wherein said suitable acylating agent is an anhydride of the formula:

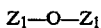

wherein $Z_1$ is —CO—R or —C(O)OR; or acyl or sulfonyl chlorides of the formula:

wherein $Z_2$ is —CO—R, —C(O)OR, or —SO$_2$R, and R is H, linear or branched $C_1$-$C_8$ alkyl, $C_3$-$C_6$ cycloalkyl, phenyl, substituted phenyl, or $C_7$-$C_{10}$ aralkyl.

21. The bis(platinum) (IV) complex of claim 1 wherein said complex is μ-(1,5-pentanediamine-N,N')bis[cis, trans-amminedichlorodiacetoxy-platinum(IV)]; μ-(1,5-pentanediamine-N,N')bis[cis, trans-amminedichlorodibutyryloxyplatinum(IV)];

μ-(1,5-pentanediamine-N,N')bis[cis, trans-amminedichlorodi(trifluoroacetoxy)platinum(IV)];

μ-(1,4-butanediamine-N,N')bis[cis, trans-amminedichlorodiacetoxy-platinum(IV)];

μ-(1,6-hexanediamine-N,N')bis[cis, trans-amminedichlorodiacetoxy-platinum(IV)];

μ-(1,6-hexanediamine-N,N')bis[cis, trans-amminedichlorodipropionylox-platinum (IV)];

μ-(1,4-butanediamine-N,N')bis[cis, trans-amminedichlorodipropionyloxy-platinum (IV)];

μ-(1,5-pentanediamine-N,N')bis[cis, trans-amminedichlorodipropionyloxy-platinum (IV)];

μ-(1,6-hexanediamine-N,N')bis[cis, trans-amminedichlorodibutyryloxy-platinum (IV)];

μ-(1,4-butanediamine-N,N')bis[cis, trans-amminedichlorodibutyryloxy-platinum (IV)];

μ-(1,5-pentanediamine-N,N')bis[cis ,trans-ammine(1,1-cyclobutanedicarboxylato(2-) -O,O')-diacetoxy-platinum(IV)];

μ-(1,5-pentanediamine-N,N')bis[cis, trans-ammine(1,1-cyclobutanedicarboxylato(2-) -O,O')-dipropionyloxy-platinum(IV)];

μ-(1,5-pentanediamine-N,N')bis[cis, trans-ammine(1,1-cyclobutanedicarboxylato(2-) O,O')-dibutyryloxy-platinum(IV)];

μ-(1,4-butanediamine-N,N')bis[cis, trans-ammine(-propanedioato(2-)-O,O')diacetoxyplatinum(IV)];

μ-(1,4-butanediamine-N,N')bis[cis, trans-ammine(-propanedioato(2-)-OO')dibutyryloxyplatinum-(IV)];

μ-(1,6-hexanediamine-N,N')bis[cis, trans-ammine(-propanedioato(2-)-O,O')dibutyryloxyplatinum-(IV)];

μ-(1,6-hexanediamine-N,N')bis[cis, trans-ammine(-propanedioato(2-)-O,O')dipropionyloxyplatinum-(IV)];

μ-(3-hydroxy-1,5-pentanediamine-N,N')bis[cis, trans-ammine(1,1-cyclobutanedicarboxylato (2-)-O,O')-diacetoxy-platinum(IV)];

μ-(3-hydroxy-1,5-pentanediamine-N,N')bis[cis, trans-ammine(propanedioato(2-) -O,O')diacetoxy-platinum (IV)];

μ-(3-hydroxy-1,5-pentanediamine-N,N')bis[cis, trans-ammine(1-ethylpropanedioato(2-) -O,O') diacetoxy-platinum(IV)];

μ-(3-hydroxy-1,5-pentanediamine-N,N')bis[cis, trans-ammine(1,1- cyclobutanedicarboxylato (2-)-O,O')-dibutyryloxy-platinum(IV)];

μ-(1,5-pentanediamine-N,N')bis[cis, trans-amminedichloroformiloxyhydroxoplatinum(IV)];

μ-(1,5-pentanediamine-N,N')bis[cis, trans-ammine(-propanedioato(2-) -O,O') diacetoxy-platinum(IV)];

μ-(1,5-pentanediamine-N,N')bis[cis, trans-ammine(-propanedioato(2-) -O,O')dipropionyloxy-platinum-(IV)]; or μ-(1,5-pentanediamine-N,N')bis[cis, trans-ammine(-propanedioato(2-) -O,O')dibutyryloxy-platinum-(IV)].

22. A pharmaceutical composition comprising an effective amount of a complex according to claim 1, in a pharmaceutically acceptable carder.

23. A method of inhibiting tumor growth in a mammal, comprising administering a tumor-inhibiting effective amount of a complex according to claim 1.

24. The bis(platinum) (IV) complex of claim 2, wherein R is methyl, ethyl, n-propyl, isopropyl, n-butyl, sec-butyl, tert-butyl, n-pentyl, n-hexyl or n-octyl.

25. The bis(platinum) (IV) complex of claim 3, wherein R is cyclopropyl, cyclobutyl, cyclopentyl or cyclohexyl.

26. The bis(platinum) (IV) complex of claim 6, wherein R is phenylmethyl, phenylethyl or phenylpropyl.

27. The bis(platinum) (IV) complex of claim 7, wherein $R_1$ is methyl, ethyl, n-propyl, isopropyl, n-butyl, sec-butyl, tert-butyl, n-pentyl, n-hexyl or n-octyl.

28. The bis(platinum) (IV) complex of claim 8, wherein $R_1$ is cyclopropyl, cyclobutyl, cyclopentyl or cyclohexyl.

29. The bis(platinum) (IV) complex of claim 9, wherein $R_1$ is methyl, ethyl, n-propyl, isopropyl, n-butyl, sec-butyl, tert-butyl, n-pentyl, n-hexyl or n-octyl.

30. The bis(platinum) (IV) complex of claim 10, wherein $R_1$ is cyclopropyl, cyclobutyl, cyclopentyl or cyclohexyl.

31. The bis(platinum) (IV) complex of claim 16, wherein said chelating dicarboxylates are oxalate, malonate, substituted malonate, succinate, glutarate or phthalate.

* * * * *